United States Patent [19]

Ebert

[11] Patent Number: 4,535,764
[45] Date of Patent: Aug. 20, 1985

[54] SURGICAL BONE TIE

[75] Inventor: Edward A. Ebert, Snyder, N.Y.

[73] Assignee: Tayco Developments, Inc., North Tonawanda, N.Y.

[21] Appl. No.: 485,449

[22] Filed: Apr. 15, 1983

[51] Int. Cl.³ .............................................. A61B 17/18
[52] U.S. Cl. ................................. 128/92 B; 128/92 E; 128/335; 24/23 EE
[58] Field of Search ..................... 128/92 B, 335, 336, 128/337, 334 R, 335.5, 339, 92 E; 24/20 R, 20 CW, 20 EE, 20 W, 23 EE, 17 R, 17 A, 17 AP, 23 B, 23 R

[56] References Cited

U.S. PATENT DOCUMENTS

| 100,897 | 3/1870 | Hunt | 24/20 EE X |
|---|---|---|---|
| 580,199 | 4/1897 | Sommerfeld | 24/20 EE |
| 1,592,897 | 7/1926 | Morton | 128/339 |
| 2,143,910 | 1/1939 | Didusch . | |
| 3,123,077 | 3/1964 | Alcamo . | |
| 3,570,497 | 3/1971 | Lemole . | |
| 3,857,396 | 12/1974 | Hardwick | 128/335 |
| 4,037,603 | 7/1977 | Wendorff . | |
| 4,119,091 | 10/1978 | Partridge . | |
| 4,201,215 | 5/1980 | Crossett et al. . | |
| 4,262,406 | 4/1981 | Fredrickson et al. | 24/23 B X |
| 4,263,904 | 4/1981 | Judet | 128/92 B |
| 4,279,248 | 7/1981 | Gabbay . | |

FOREIGN PATENT DOCUMENTS 122158   1/1972   Denmark .............................. 128/335

Primary Examiner—Michael H. Thaler
Attorney, Agent, or Firm—Joseph P. Gastel

[57] ABSTRACT

A surgical bone tie for securing separated sections of bone including a needle for penetrating the separated sections after they have been placed in juxtaposition, a cutting member at the trailing end of the needle for cutting a hole of rectangular cross section as the needle is pulled through the bone, a flexible metal band of rectangular cross section attached to the trailing end of the cutting member to fit into the hole formed by the cutting member, and a flat locking member at the trailing end of the band having a plurality of holes for receiving an intermediate portion of the band and securing this intermediate portion of the band to the locking member, with portions of the band lying above the flat locking member to hold it flat against the bone and with the free end of the band remaining after the needle was cut therefrom being concealed underneath a portion of the locking member so as not to provide an exposed sharp end.

18 Claims, 18 Drawing Figures

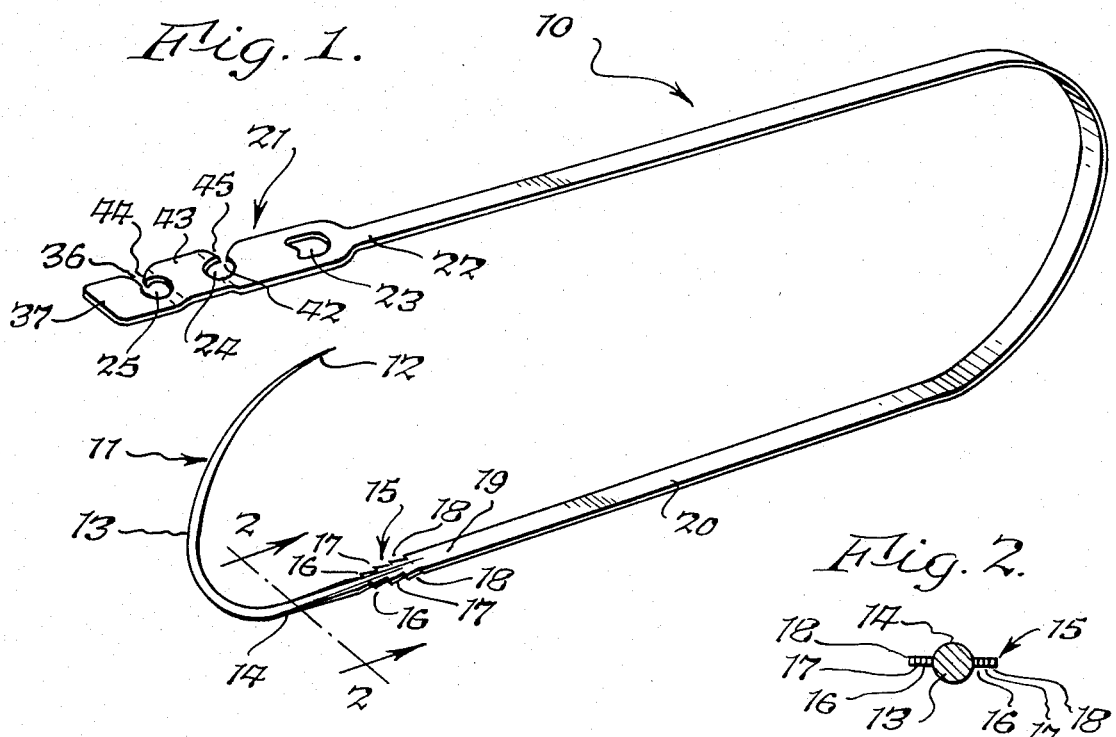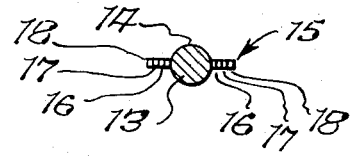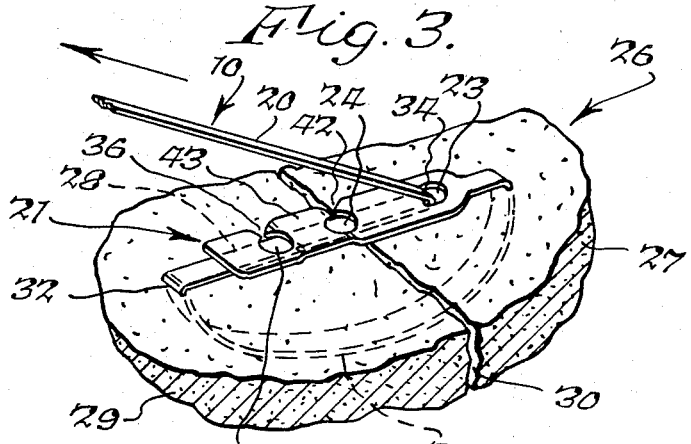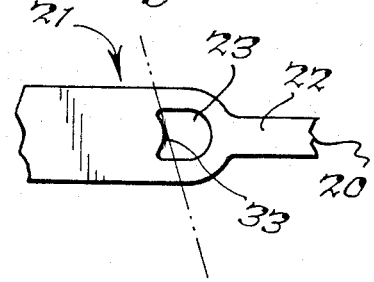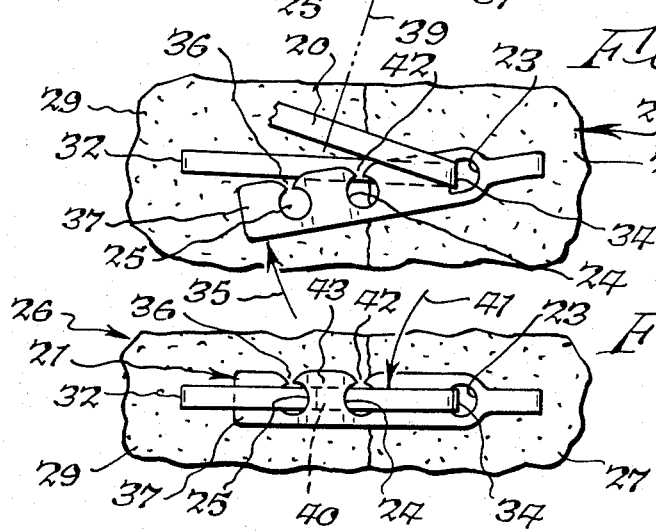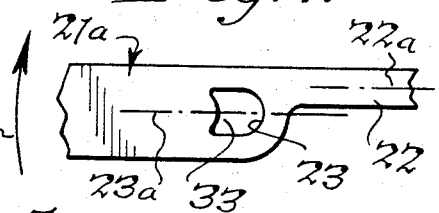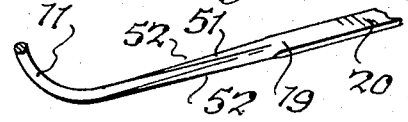

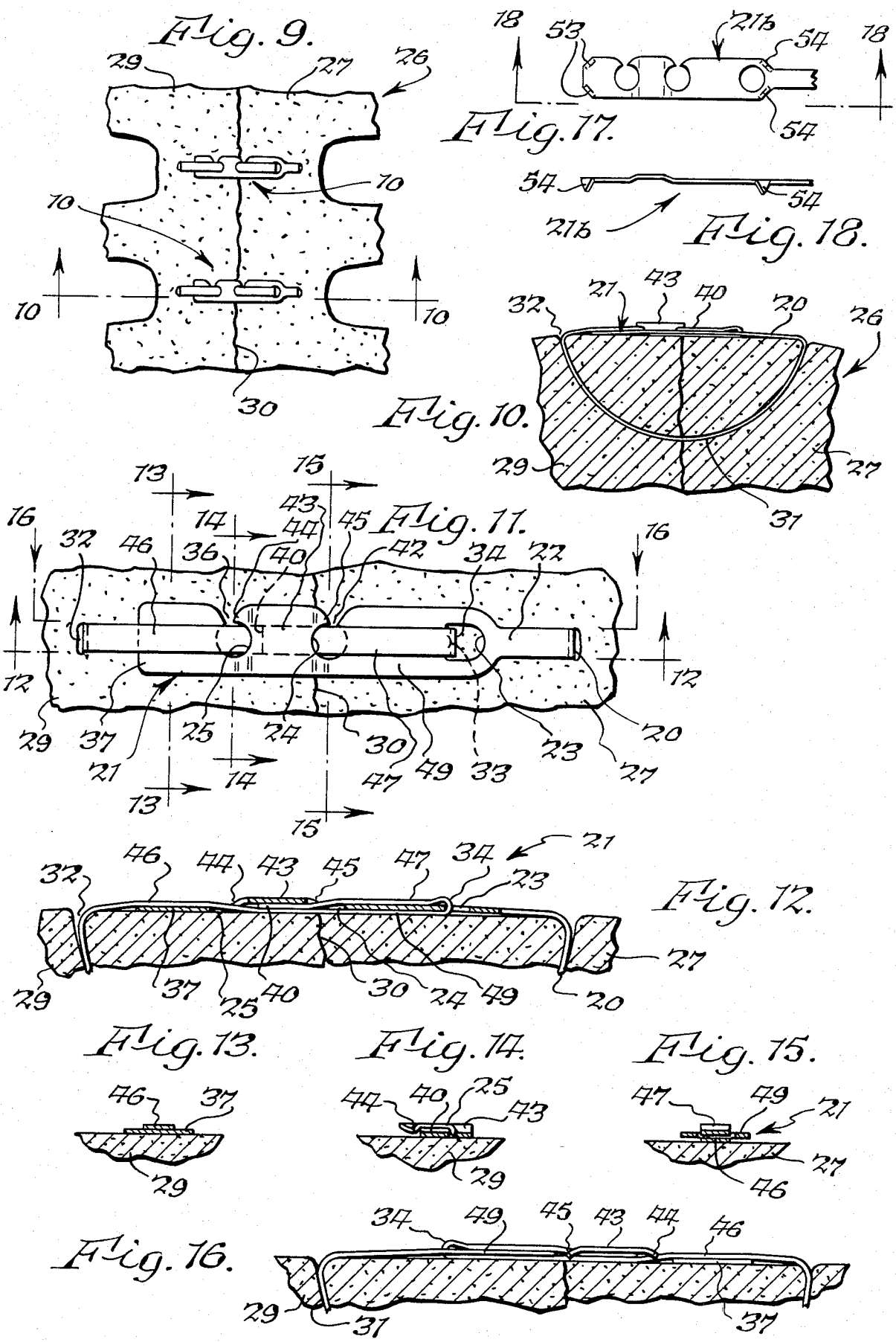

SURGICAL BONE TIE

BACKGROUND OF THE INVENTION

The present invention relates to an improved surgical bone tie for use in surgical procedures in connecting adjacent portions of bones which have been separated.

By way of background, in open-heart surgery the sternum is severed longitudinally to obtain access to the chest cavity. In the past, one method of securing the severed portions of the sternum to each other utilized surgical wires. However, the use of such wires was not satisfactory because they acted in the nature of a cheese cutter to cut through the bone when the bone was subjected to a separating force. In addition, twisting the free ends of the wires to secure them created a sharp barb which tore the skin. Furthermore, devices such as shown in U.S. Pat. Nos. 4,201,215 and 4,279,248 were proposed. However, these were deficient for a number of reasons, namely, their complexity and further because they exerted pressure on blood vessels which are located on the underside of the sternum.

SUMMARY OF THE INVENTION

It is the object of the present invention to provide an improved surgical bone tie which will provide a relatively broad bearing surface which will not cut through sections of bone which it joins and which can be securely installed in an extremely simple and efficient manner and which can be locked in place without producing sharp edges. Other objects and attendant advantages of the present invention will readily be perceived hereafter.

The present invention relates to a surgical bone tie comprising a needle having a leading end for penetrating adjacent bone sections, a trailing end on said needle, a cutting section of a first cross section adjacent said trailing end of said needle for shaping the holes in the bone sections penetrated by said needle to include the shape of said first cross section, a substantially flat band having a second cross section for fitting within said holes of said first cross section, a leading end on said band secured proximate said cutting section, a trailing end on said band, and a substantially flat locking member having a leading end and a trailing end, said leading end of said locking member being secured to said trailing end of said band, locking means on said locking member for receiving an intermediate portion of said band between said leading and trailing ends of said band in locking engagement with said locking member, said locking means including means for causing said locking member to extend in alignment with said intermediate portion of said band after said intermediate portion of said band has been locked thereto and for causing said intermediate portion of said band and said locking member to lie flat against a portion of said bone sections.

The various aspects of the present invention will be more fully understood when the following portions of the specification are read in conjunction with the accompanying drawings wherein:

BRIEF DESCRIPTION OF THE DRAWINGS

FIG. 1 is a perspective view of the surgical bone tie which includes a curved needle, broach portion, band portion and a locking portion;

FIG. 2 is a cross sectional view taken substantially along line 2—2 of FIG. 1;

FIG. 3 is a fragmentary perspective view showing the surgical bone tie which has been threaded through to adjacent portions of a previously severed sternum, with the surgical bone tie assuming a partially completed locking condition;

FIG. 4 is a fragmentary plan view of the surgical bone tie in one of the positions which it assumes during the locking operation;

FIG. 5 is a view similar to FIG. 4 and showing the free end of the band, after the needle end has been severed, after it has been swung into position underlying a portion of the locking member;

FIG. 6 is a fragmentary plan view of the locking member showing the convexly curved border of the aperture which receives the band;

FIG. 7 is a fragmentary plan view similar to FIG. 6 but showing a modified connection between the trailing end of the band and the locking member;

FIG. 8 is a fragmentary perspective view of a modified form of cutting member which can replace the broach of FIG. 1;

FIG. 9 is a fragmentary plan view of the severed portions of a sternum which have been joined together by surgical bone ties of the present invention which are spaced between the ribs;

FIG. 10 is a fragmentary cross sectional view taken substantially along line 10—10 of FIG. 9;

FIG. 11 is an enlarged fragmentary plan view of the surgical bone ties shown in FIGS. 5 and 9;

FIG. 12 is a fragmentary cross sectional view taken substantially along line 12—12 of FIG. 11;

FIG. 13 is a fragmentary cross sectional view taken substantially along line 13—13 of FIG. 11;

FIG. 14 is a fragmentary cross sectional view taken substantially along line 14—14 of FIG. 11;

FIG. 15 is a fragmentary cross sectional view taken substantially along line 15—15 of FIG. 11;

FIG. 16 is a fragmentary cross sectional view taken substantially along line 16—16 of FIG. 11;

FIG. 17 is a fragmentary plan view of a modified locking member; and

FIG. 18 is a fragmentary side elevational view taken substantially in the direction of arrows 18—18 of FIG. 17.

DESCRIPTION OF THE PREFERRED EMBODIMENTS

The improved surgical bone tie 10 of the present invention includes a curved needle 11 having a leading pointed end 12 which merges into a curved central portion 13 which in turn merges into a trailing end 14. A broach 15 is suitably secured to the trailing end 14. As can be seen from FIG. 2, needle 13 is circular in cross section and the teeth 16, 17 and 18 of the broach will generate a rectangular hole. The leading end 19 of metal band 20 is suitably secured to the trailing end of broach 15. Band 20 is substantially rectangular in cross section and is of a size to fit snugly in the rectangular hole created by broach 15. Band 20 is of a sufficient length to pass through adjacent portions of bone to be joined with a sufficient extra length to permit manipulation of the band for tying purposes. A locking member 21 is secured to the trailing end 22 of band 20. Locking member 21 can be formed integrally with band 20, and it is wider than band 20. Locking member 21 includes apertures 23, 24 and 25.

As is conventional in open-heart surgery and similar types of surgery where entry has to be obtained to the chest cavity, the sternum 26 is cut longitudinally so that it is divided into parts 27 and 29, the cut being depicted by numeral 30. After the surgery has been completed, the two sections 27 and 29 have to be tied together. Tie 10 is used for this purpose. The pointed end 12 of needle 11 is forced through section 27 and then through section 29 as the two sternum halves are held in mating engagement. The needle has the desired curvature, and it will generate a path 31 through which the broach 15 will follow to form a shaped perforation which will receive band 20 with a snug fit. The band 20 is pulled through path 31 until such time as a sufficient length of band has been pulled out of sternum section 29 at 32 to permit needle 13 to be threaded through aperture 23 so that an intermediate portion of band 20 can be passed through aperture 23. Thereafter, locking member 21 is pressed against the two sternum halves 26 and 29 to the position shown in FIG. 3 and band 20 is pulled taut. While locking member 21 is held in the position shown in FIG. 3, band 20 is bent so that it bears against convex edge 33 (FIG. 6) of aperture 23. This will determine the tightness of the band. Convex edge 33 permits rocking of locking member 21 to the position of FIG. 4 and thereafter back to the position of FIG. 5. Furthermore, the central portion of convex edge 33 will be bearing against band 20, thereby obviating the possibility that the band 20 could be torn if a circular aperture 23 were used, in which event the spaced edges of the circular aperture could possibly cut into the outer edges of band 20. Pulling the band through the opening 25 around the edge 33 to tighten the band and then bring it into a bent position, as at 34, work hardens the metal in this area to form a strong crease at the bend 34 which is resistant to reversal, thereby providing a strong lock.

After the surgical bone tie 10 has assumed the position in FIG. 3, there will be a portion 28 of the band tie between aperture 32 and bend 34 in underlying relationship to locking member 21. The locking member 21 is thereafter swung laterally from the position of FIG. 3 to the position of FIG. 4. Thereafter, locking member 21 is swung in the direction of arrow 35 so that band 20 will pass through slot 36 and enter aperture 25 so that the trailing end portion 37 of locking band 21 will lie under band 20, as shown in FIG. 5. This will tightly secure the surgical bone tie in locked position flat against the bone. Thereafter, band 20 is severed at cut line 39 to provide a free end 40. The free end of band 20 is then swung in the direction of arrow 41 through slot 42 and into aperture 24. Thus, the central portion 43 of the locking member between apertures 24 and 25 will overlie the extreme sharp end 40 of band 20, serving the dual purpose of securely locking the band in position and covering the free sharp end 40 which could cut the flesh. The edges 44 and 45 adjacent slots 36 and 42, respectively, are bent downwardly (FIGS. 1, 3, 12 and 14) to retain the portions of band 20 passing through apertures 24 and 25 from swinging outwardly after they have been placed in the position shown in FIGS. 5 and 11. The connecting of the intermediate portion of the band to locking member 21 by inserting it through the holes in the locking member will cause the intermediate portion of the band and the locking member to extend in alignment with each other.

As can be seen from the drawings, it is an intermediate portion of band 20, that is, a portion between the leading end 19 and trailing end 22, which coacts with locking member 21 to secure the surgical bone tie in locking condition. Of the intermediate portion, band portion 46 (FIG. 11) overlies locking member portion 37, and band portion 47 overlies locking member portion 49. As can be seen clearly in FIGS. 12, 14 and 16, the portion of the band at 43 is located at a higher elevation than the adjacent portions of the locking member to receive the two band thicknesses underneath it.

In FIG. 7 a modified locking member 21a is disclosed for attachment to the terminal end 22 of band 20. Locking member 21a is identical to locking member 21 in all respects except that it is connected to band 20 in an offcenter fashion as shown by the centerline 22a being offset from the centerline 23a so that when it is tightened it will be biased in the direction of arrow 50 so as to tend to maintain the locked relationship between the band and the locking member. In other words, the bias is such so as to force band 20 into holes 24 and 25 rather than out of them.

In FIG. 8 a modified hole cutting arrangement is shown wherein a knife 51 having opposed cutting edges 52 is used instead of broach 15.

In FIGS. 17 and 18 a modified locking member 21b is disclosed which is identical in all respects to locking member 21 except that spikes 53 are formed at the outer end of portion 37 and mirror image spikes 54 are formed proximate end 22 of the band. The spikes will aid in maintaining locking member 21a in the position of FIG. 5 during tightening of the band.

The needle 13 is fabricated from steel having a predetermined curvature so as to provide the desired path through the adjacent sections of bone, and this curvature may be varied for different applications. The band 20 is fabricated of surgical stainless steel and it may have a width of between 1/16 and ⅛ of an inch and a thickness of between 0.003 inches and b 0.006 inches, depending on the hardness or stiffness of the steel. The needle diameter could be of a maximum diameter of about 0.045 inches. It will be appreciated that other dimensions for the various components can be used, as required for various applications. It will further be appreciated that under certain circumstances the band and the locking member could be fabricated from suitable structural plastic. In addition, while the surgical bone tie has been demonstrated for use in attaching severed sections of a sternum, it will be appreciated that it can be used to attach other bones which have been separated. In addition, while a needle 11 with a pointed end has been disclosed, it will be appreciated that the path for band 20 can be generated by a separate instrument so as to obviate the need for a sharp pointed needle, in which event a lead-in portion in the nature of a needle need be secured to band 20, and this structure is contemplated by the claims.

While preferred embodiments of the present invention have been disclosed, it will be understood that the present invention is not limited thereto, but may be otherwise embodied within the scope of the following claims.

What is claimed is:

1. A surgical bone tie comprising a needle having a leading end for penetrating adjacent bone sections of a bone, a trailing end on said needle, a cutting section of a first cross section adjacent said trailing end of said needle for shaping the holes in the bone sections penetrated by said needle to include the shape of said first cross section, a substantially flat band having a second cross section for fitting within said holes of said first cross section, a leading end on said band secured proximate said cutting section, a trailing end on said band, and a substantially flat locking member having a leading end and a trailing end, said leading end of said locking member being secured to said trailing end of said band, locking means on said locking member for receiving an intermediate portion of said band between said leading and trailing ends of said band in locking engagement with said locking member, said locking means including means for causing said locking member to extend in alignment with said intermediate portion of said band after said intermediate portion of said band has been locked thereto and for causing said intermediate portion of said band and said locking member to lie flat against a portion of said bone.

2. A surgical bone tie as set forth in claim 1 wherein said cutting section comprises a broach.

3. A surgical bone tie as set forth in claim 1 wherein said cutting section comprises a knife edge.

4. A surgical bone tie as set forth in claim 1 wherein said second cross section is rectangular.

5. A surgical bone tie as set forth in claim 1 wherein said locking member is of greater width than said intermediate portion of said band, and wherein said locking means comprise aperture means in said band for receiving said intermediate portion of said band with said intermediate portion of said band holding said locking member flat against at least one of the bone sections and with said locking member concealing a severed end of said band.

6. A surgical bone tie as set forth in claim 5 wherein said aperture means comprises a first aperture proximate said trailing end of said band, a second aperture remote from said trailing end of said band, and a third aperture intermediate said first and second apertures, a first locking member portion between said first and third apertures, a second locking member portion between said second and third apertures, and a third locking member portion between said third aperture and said trailing end of said locking member, said intermediate portion of said band including a first portion which overlies said third locking member portion and a second portion which passes through said second aperture and a third portion which extends under said second and first locking member portions and a fourth portion which extends through said first aperture and a fifth portion which overlies said first locking member portion, and an outer end portion which extends through said third aperture and which includes an outer end which lies underneath said second locking member portion and between said second locking member portion and said band.

7. A surgical bone tie as set forth in claim 6 wherein said free outer end includes an exteme outer end portion which is completely concealed by said second locking member portion.

8. A surgical bone tie as set forth in claim 6 wherein said locking member comprises a flat band having outer sides, and slot means extending between said at least one of said sides and said second and third apertures.

9. A surgical bone tie as set forth in claim 8 including means on said locking member proximate said slot means for holding said intermediate portion of said band against movement therethrough out of said second and third apertures.

10. A surgical bone tie as set forth in claim 9 wherein said locking member includes an upper side and underside, and spike means extending from said underside for effecting locking engagement between said locking member and at least one of said bone sections.

11. A surgical bone tie as set forth in claim 6 wherein said first aperture includes a portion closest to said third aperture which is bounded by a convex edge.

12. A surgical bone tie as set forth in claim 1 wherein said locking member includes an upper side and underside, and spike means extending from said underside for effecting locking engagement between said locking member and at least one of said bone sections.

13. A surgical bone tie for joining adjacent bone sections of a bone comprising a substantially flat band having a leading end on said band, a trailing end on said band, and a substantially flat locking member having a leading end and a trailing end, said leading end of said locking member being secured to said trailing end of said band, locking means including aperture means within said locking member for receiving therein an intermediate portion of said band between said leading and trailing ends of said band in locking engagement with said locking member, said locking means including means for causing said locking member to extend in alignment with said intermediate portion of said band after said intermediate portion of said band has been locked thereto and for causing said intermediate portion of said band and said locking member to lie flat against a portion of said bone, said locking member being of greater width than said intermediate portion of said band, and said aperture means receiving said intermediate portion of said band with said intermediate portion of said band holding said locking member flat against at least one of the bone sections and with said locking member concealing a severed end of said band, said aperture means comprising a first aperture proximate said trailing end of said band, a second aperture remote from said trailing end of said band, and a third aperture intermediate said first and second apertures, a first locking member portion between said first and third apertures, a second locking member portion between said second and third apertures, and a third locking member portion between said third aperture and said trailing end of said locking member, said intermediate portion of said band including a first portion which overlies said third locking member portion and a second portion which passes through said second aperture and a third portion which extends under said second and first locking member portions and a fourth portion which extends through said first aperture and a fifth portion which overlies said first locking member portion, and an outer end portion which extends through said third aperture and which includes an outer end which lies underneath said second locking member portion and between said second locking member portion and said band.

14. A surgical bone tie as set forth in claim 13 wherein said free outer end includes an extreme outer end portion which is completely concealed by said second locking member portion.

15. A surgical bone tie as set forth in claim 13 wherein said locking member comprises a flat band having outer sides, and slot means extending between said at least one of said sides and said second and third apertures.

16. A surgical bone tie as set forth in claim 13 wherein said first aperture includes a portion closest to said third aperture which is bounded by a convex edge.

17. A surgical bone tie comprising a needle having a leading end for penetrating adjacent bone sections of a bone, a trailing end on said needle, a cutting section of a first cross section adjacent said trailing end of said needle for shaping the holes in the bone sections penetrated by said needle to include the shape of said first cross section, a substantially flat band having a second cross section for fitting within said holes of said first cross section, a leading end on said band secured proximate said cutting section, a trailing end on said band, and a substantially flat locking member having a leading end and a trailing end, said leading end of said locking member being secured to said trailing end of said band, locking means on said locking member for receiving an intermediate portion of said band between said leading and trailing ends of said band in locking engagement with said locking member, and means operatively associated with said locking means for concealing a free end of said intermediate portion of said band which is produced after said intermediate portion of said band has been severed.

18. A surgical bone tie as set forth in claim 17 including means operatively associated with said locking member for causing said intermediate portion of said band and said locking member to lie flat against a portion of said bone.

* * * * *